United States Patent
Sherman et al.

[11] Patent Number: 5,954,725
[45] Date of Patent: *Sep. 21, 1999

[54] MULTI-ANGLE BONE SCREW ASSEMBLY USING SHAPE MEMORY TECHNOLOGY

[75] Inventors: Michael C. Sherman; Troy Drewry, both of Memphis, Tenn.

[73] Assignee: SDGI Holdings, Inc., Wilmington, Del.

[*] Notice: This patent is subject to a terminal disclaimer.

[21] Appl. No.: 09/042,911

[22] Filed: Mar. 17, 1998

Related U.S. Application Data

[63] Continuation of application No. 08/744,403, Nov. 7, 1996, Pat. No. 5,728,098.

[51] Int. Cl.⁶ .................................................. A61B 17/70
[52] U.S. Cl. ................................ 606/78; 606/61; 606/73
[58] Field of Search .................................. 606/60, 61, 72, 606/73, 76, 78; 411/909

[56] References Cited

U.S. PATENT DOCUMENTS

| | | | |
|---|---|---|---|
| 3,740,839 | 6/1973 | Otte et al. | 29/628 |
| 4,946,458 | 8/1990 | Harms et al. | 606/61 |
| 5,443,467 | 8/1995 | Biedermann et al. | 606/65 |
| 5,474,555 | 12/1995 | Puno et al. | 606/73 |
| 5,549,608 | 8/1996 | Errico et al. | 606/61 |
| 5,551,871 | 9/1996 | Besselink et al. | 443/5 |
| 5,554,157 | 9/1996 | Errico et al. | 606/61 |
| 5,575,792 | 11/1996 | Errico et al. | 606/61 |
| 5,578,033 | 11/1996 | Errico et al. | 606/61 |
| 5,584,834 | 12/1996 | Errico et al. | 606/61 |
| 5,586,984 | 12/1996 | Errico et al. | 606/61 |
| 5,683,404 | 11/1997 | Johnson | 606/151 |

FOREIGN PATENT DOCUMENTS

| | | | |
|---|---|---|---|
| 2725892 A1 | 4/1996 | France | A61B 17/70 |

OTHER PUBLICATIONS

"Some Applications of Shape–Memory Alloys" C.M. Wayman, University of Illinois at Urbana–Champaign; Journal of Metals, Jun. 1980.

*Primary Examiner*—Micheal Buiz
*Assistant Examiner*—David O. Reip
*Attorney, Agent, or Firm*—Woodard, Emhardt, Naughton Moriarty & McNett Patent and Trademark Attorneys

[57] ABSTRACT

In one embodiment, a spinal fixation assembly includes an elongated member, such as a spinal rod, configured for placement adjacent the spine and a bone engaging fastener, such as a bone screw having a lower portion configured for engaging a vertebra and a head that is at least partially spherical. The assembly further includes a receiver member defining a bore therethrough from a top end to a bottom end, a recess for receiving the head of the bone screwing fastener therein, and a lower opening at said bottom end of the receiver member through which the bone screw extends. The recess is configured to at permit pivoting of the bone screw within the receiver member until the head is fixed within the recess. The receiver member also includes a channel communicating with the bore and having an upper opening at the top end of the receiver member for insertion of the spinal rod into the channel. In one embodiment, two compression members are provided, each being formed of a temperature responsive material and having a first configuration at a first temperature and a different second configuration at a different second temperature in which the compression member contracts about a portion of the receiver member to thereby compress the receiver member about both the head of the bone screw within the recess and the spinal rod within the channel.

24 Claims, 4 Drawing Sheets

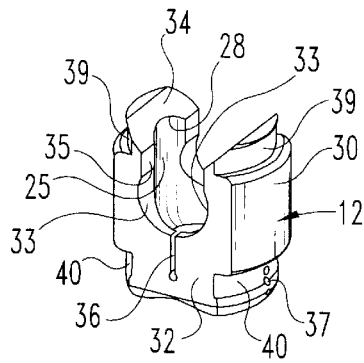
Fig. 6
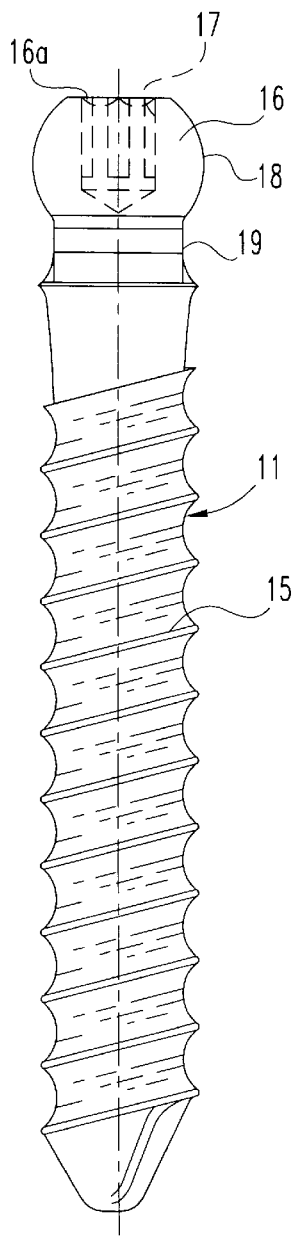
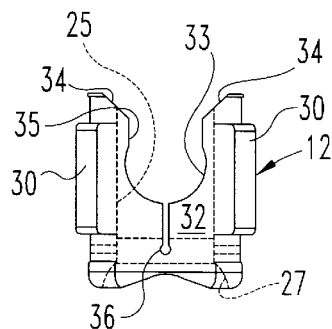
Fig. 7
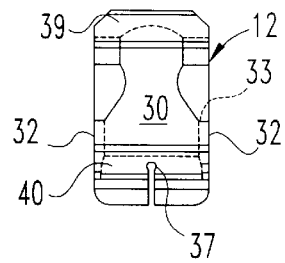
Fig. 8
Fig. 5
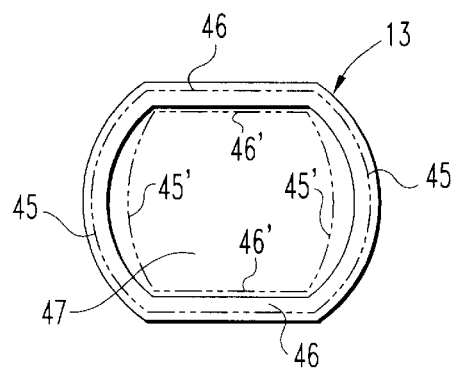
Fig. 9

MULTI-ANGLE BONE SCREW ASSEMBLY USING SHAPE MEMORY TECHNOLOGY

This application is a continuation of application Ser. No. 08/744,403, filed Nov. 7, 1996, now U.S. Pat. No. 5,728,098.

BACKGROUND OF THE INVENTION

The present invention concerns a bone screw assembly, and particularly an assembly useful for engagement in the vertebrae of the spine. The invention contemplates an assembly that is capable of supporting a bone engaging fastener at multiple angular orientations with respect to an elongated member extending along the spine.

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another very prevalent fixation element is a spinal screw which can be threaded into various aspects of the vertebral bone.

In one typical procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to these plurality of bone screws to apply corrective and stabilizing forces to the spine.

One example of a rod-type spinal fixation system is the TSRH® Spinal System sold by Danek Medical, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/CD Spinal System sold by Sofamor Danek Group, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Dr. Cotrel. One benefit of this feature of the CD® System is that the fixation element is positioned directly beneath the elongated rod. This helps reduce the overall bulkiness of the implant construct and minimizes the trauma to surrounding tissue.

On the other hand, these fixation elements of the CD® System are capable only of pivoting about the spinal rod to achieve variable angular positions relative to the rod. While this limited range of relative angular positioning is acceptable for many spinal pathologies, many other cases require more creative orientation of a bone screw, for instance, relative to a spinal rod. Certain aspects of this problem are addressed by the variable angle screw of the TSRH® System, as discussed in the '909 Patent. However, there is a need for a bone screw that is capable of angular orientation in multiple planes relative to the spinal rod. Preferably, the bone screw is capable of various three-dimensional orientations with respect to the spinal rod. Screws of this type have been referred to as poly-axial or multi-axial bone screws.

Others have approached the solution to this problem with various poly-axial screw designs. For example, in U.S. Pat. No. 5,466,237 to Byrd et al., a bone screw is described which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

The same inventors implemented a somewhat different approach in U.S. Pat. No. 5,474,555. In this patent, an anchor receives a semi-spherical head of a bone screw within a recess. The anchor includes a rod channel transverse to the screw recess. The anchor is externally threaded to receive an internally threaded nut. In one embodiment, the nut is threaded directly down onto the spinal rod to clamp the rod within the channel. In another embodiment, a cap is provided between the rod and nut. In both embodiments, neither the rod nor the external not impart any clamping force onto the head of the bone screw.

In another approach shown in U.S. Pat. No. 4,946,458 to Harms et al., a spherical headed bone screw is supported within separate halves of a receiver member. The bottom of the halves are held together by a retaining ring. The top of the receiver halves are compressed about the bone screw by nuts threaded onto a threaded spinal rod. In another approach taken by Harms et al., in U.S. Pat. No. 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threaded rods can tend to weaken the rods in the face of severe spinal loads. Moreover, the design of the bone screws in the '458 and '678 Patents require a multiplicity of parts and are fairly complicated to achieve complete fixation of the bone screw.

Two patents to Errico et al., U.S. Pat. Nos. 5,549,608 and 5,554,157, depict two alternative approaches to multi-angle bone screw apparatus. The '608 Patent describes a complicated array of components that includes a tapered lower portion defining a spherical recess to receive the head of a bone screw. The lower portion is slotted so that the lower portion can be compressed about the bone screw head by operation of a ring pushed down the tapered lower portion. A hollow cylindrical rod securing sleeve fits over an upper portion of the coupling element that is operable to clamp the rod within the coupling element as the sleeve is pushed down onto the ring. The coupling element includes a threaded post onto which a nut is threaded that is operable to push the sleeve down onto the rod and onto the ring to compress the lower portion against the bone screw head. Like the Harms devices described above, the approach in the '608 Patent involves a multiplicity of parts and excessive "fiddle factor" for use in a spinal surgery.

The second alternative in the Errico '157 Patent is similar to the approach taken in the Puno '555 Patent, except that the rod contacts the spherical head of the bone screw in the '157 Patent. An external nut is threaded directly down onto the spinal rod which then bears directly on the bone screw head to clamp the head within a spherical recess. While this design offers much greater simplicity than the Errico '608 Patent it suffers from the point contact between the rod and the spherical head of the bone screw. It is uncertain whether this clamping mechanism is sufficient to maintain the relative position between bone screw and spinal rod under severe spinal loads.

In recent years, a special material known as "shape-memory alloy" has found its way into the field of medical devices. These materials are alloys of known metals, such as copper and zinc, nickel and titanium, silver and cadmium, and others, that are known to exhibit a "shape-memory" in which a particular component formed of a shape-memory alloy (SMA) will change shape upon changes in temperature.

The shape-memory characteristics of SMAs occur when the alloy changes from a martensitic crystal phase to an austenitic crystal phase. In the martensitic stage, the SMA is relatively weak and pliable. As the temperature of the SMA component is increased above a transformation temperature range, the SMA transforms to its austenitic phase in which the material is relatively strong with super-elastic properties. Generally, the strength and super-elastic characteristics of an SMA tend to increase toward the high temperature end of the transformation temperature range and decrease toward the low temperature end.

In use, an object made of an SMA is formed into a particular shape at a temperature that is either above or below the transformation temperature range. The object will then change shape as its temperature increases or decreases through that transformation temperature range. In the field of medical devices, a device is formed into its in situ shape at the high temperature, or the temperature above the transformation temperature range. The device is then cooled to be provided to the surgeon for implantation. One known application of SMA technology in the medical field is a vena cava filter that assumes a smaller shape at its low temperature, and then expands to its larger shape within a blood vessel when heated to body temperature.

While there are many alloys that exhibit shape memory characteristics, one of the more common SMAs in the medical field is an alloy of nickel and titanium. One such well known alloy is Nitinol®, which has proven highly effective for devices placed within the human body because its transformation temperature range falls between room temperature and normal human body temperature. Shape-memory technology has also found its way into the field of orthodontics, as described in U.S. Pat. No. 5,551,871 to Besselink et al. This patent describes face bow head gear used for aligning teeth of a patient in which an SMA wire is used to align and hold the teeth of a patient. The '871 Patent also discloses devices for use in treating scoliosis including a transverse connector and bone engaging fasteners that clamp to an elongated rod by way of shape-memory characteristics. While the '871 Patent shows one use of SMA technology for spinal hooks and screws, the hooks and screws are only capable of pivoting about the axis of the rod. In this regard, the devices shown in the '871 Patent are similar to the components of the CD® System discussed above.

There is a need remaining in the industry for a multi-axial or poly-axial bone screw that can be readily and securely engaged to an elongated spinal rod. Preferably, the spinal rod can be of any configuration—i.e., smooth, roughened, knurled or even threaded.

This need also encompasses the goal of minimizing the profile and bulk of any of the components used to engage the bone screw to the spinal rod in a variety of angular orientations. Moreover, it is desirable to reduce the number of components of the system that must be manipulated by the surgeon during a surgical procedure.

DESCRIPTION OF THE FIGURES

FIG. 5 is a side elevational view of a bone screw adapted for use with the multi-axial screw assembly shown in FIG. 1.

FIG. 6 is a top perspective view of a receiver member used with the multi-axial screw assembly shown in FIG. 1.

FIG. 7 is a side elevational view of the receiver member shown in FIG. 6.

FIG. 8 is an end elevational view of the receiver member shown in FIG. 6.

FIG. 9 is a top elevational view of a locking ring used with the multi-axial screw assembly shown in FIG. 1.

SUMMARY OF THE INVENTION

Figure 1:
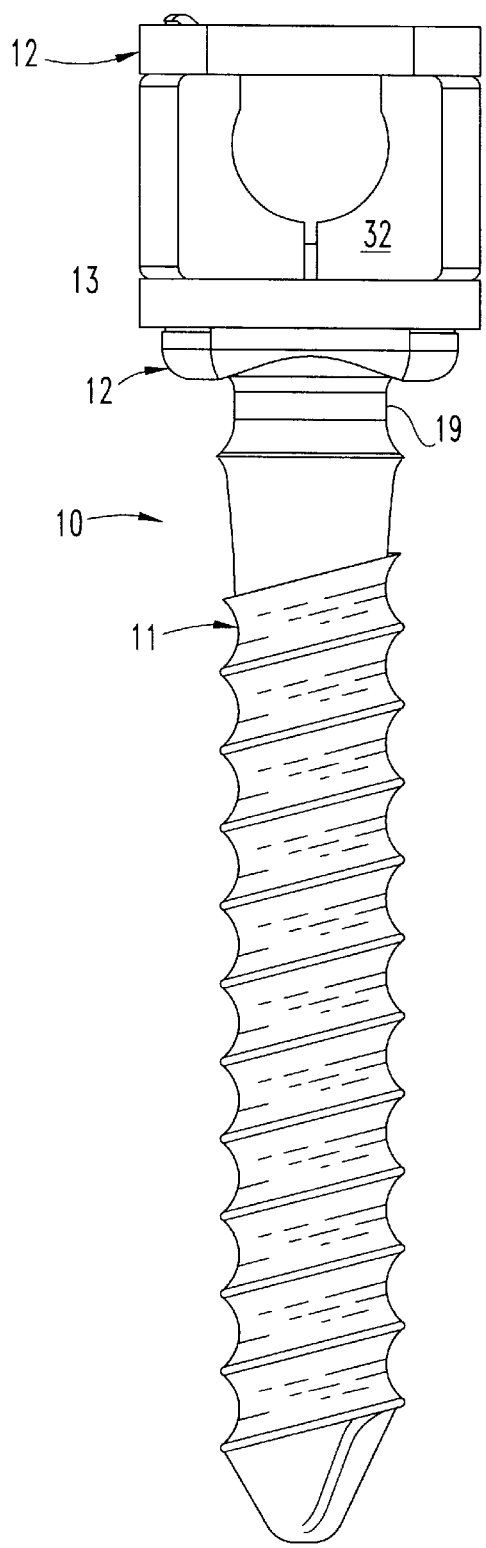
FIG. 1 is a side elevational view of a multi-axial screw assembly according to one embodiment of the present invention.

The deficiencies of prior bone screws are addressed by several aspects of the present invention. In one embodiment of the invention, a spinal fixation assembly is provided which includes a bone engaging fastener, such as a bone screw, and an elongated member, such as a spinal rod. The fixation assembly includes a multi-axial screw assembly that permits fixation of the bone screw to the spinal rod at any of a plurality of angles in three-dimensional space relative to the rod. In other words, the bone screw can pivot relative to the rod about a cone directly beneath the spinal rod. In one aspect of the invention, the bone screw includes a head that is at least partially spherical. The head is preferably truncated to form a flat upper surface within which a tool engaging recess is defined.

The multi-axial screw assembly further includes a receiver member defining a bore therethrough from its top end to its bottom end. The bore further includes a recess for receiving the head of the bone screw, with a lower opening at the bottom end of the receiver member through which a lower portion of the bone screw extends to engage the spine. The receiver member also includes a channel transverse to the bore and communicating with the bore to receive the spinal rod. Both the bone screw and the spinal rod can be inserted into the receiver member through an upper opening.

In a further aspect of the invention, a locking ring is provided at the bottom of the receiver member. The locking ring is configured to closely fit around the perimeter of the receiver member and particularly overlapping the recess within which the head of the bone screw resides. In accordance with the invention, the locking ring is formed of a shape-memory alloy (SMA) configured so that the locking ring has a first diameter that is larger than a second diameter, and in which the locking ring transforms from the first diameter to the second diameter when heated to the body temperature of the patient. In other words, the locking ring contracts with increasing temperature so that the ring presses the receiver member against the head of the bone screw, thereby clamping the bone screw within the multi-axial screw assembly.

In a further feature of the invention, the receiver member includes thin slots on opposite sides of the receiver to facilitate compression of the receiver member about the head of the bone screw. In another aspect, opposite slots are provided in the receiver member that are offset by 90° from the other slots. These slots extend into the channel within which the spinal rod is received. A second SMA locking ring is disposed over the top of the receiver member to apply a clamping force from the top of the receiver member. In this manner, the spinal rod can be engaged by the receiver member as the upper SMA locking ring transforms to its austenitic shape.

In another embodiment, the receiver member is modified to permit entry of the bone screw head from the bottom of the receiver member. In this embodiment, the receiver member is provided with a plurality of slots emanating from the bottom of the member. The recess within the member is enlarged adjacent the bottom of the receiver member to accept the bone screw head by expansion of the receiver member at the slots. The slots terminate adjacent the rod channel so that transformation of the lower SMA ring will provide some clamping force to the spinal rod. In addition, the upper portion of the receiver member will provide further clamping force upon temperature transformation of the upper SMA ring.

The present invention provides an assembly that permits fixation of a bone engaging fastener to an elongated member at a plurality of three-dimensional angular orientations relative to the elongated member. The preferred embodiments of the inventive multi-axial screw assembly provides the advantage of a solid fixation between a spinal rod and a bone screw, regardless of the angle between the two components.

A further benefit of the present invention resides in the minimum number of components necessary to effect this solid fixation. Yet another benefit is achieved by the use of shape-memory technology to eliminate the need for extra mechanical fasteners and engagement instruments that are prevalent with prior devices.

It is one object of the invention to provide an assembly that allows for solid fixation of a fastener at a wide range of three-dimensional angles relative to an elongated component. Another object is to provide such an assembly that has minimum prominence and minimum bulk, and that readily supports the bone engaging fastener directly beneath the elongated member. Other objects and benefits of the inventions will become apparently upon consideration of the following written description and accompanying figures illustrating one embodiment of the invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
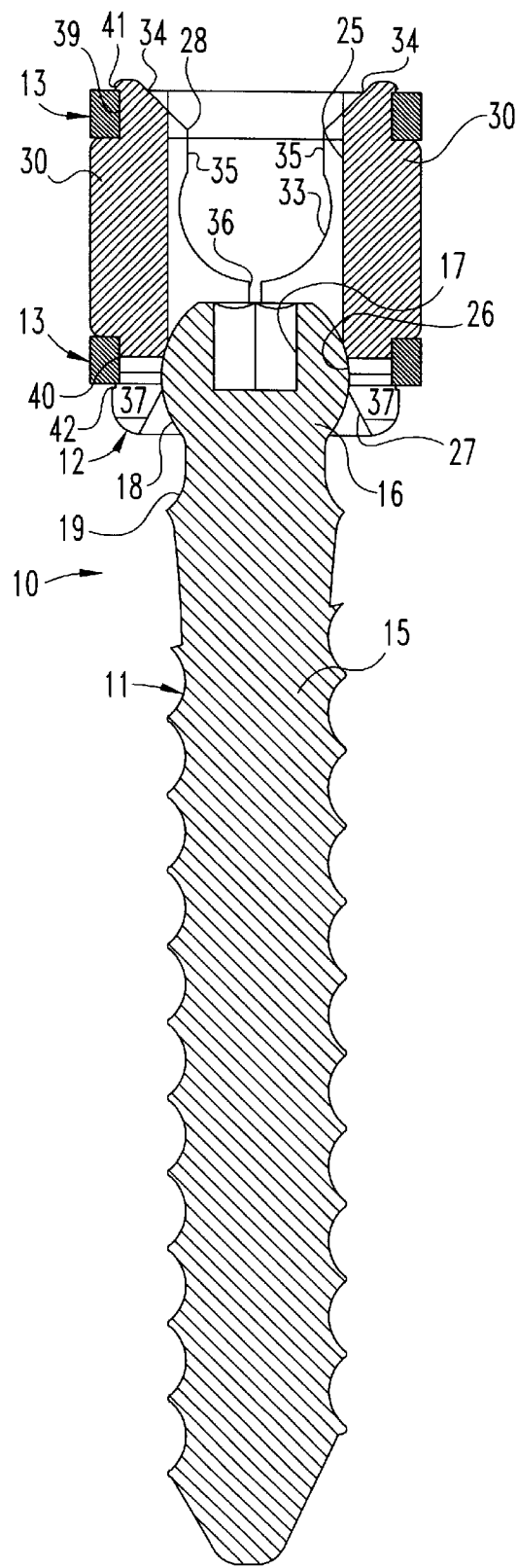
FIG. 2 is a side cross-sectional view of the screw assembly depicted in FIG. 1.

In one aspect of the invention, a spinal fixation assembly includes an elongated member, such as the spinal rod, and a multi-axial screw assembly, such as the assembly 10 shown in FIGS. 1 and 2. The spinal fixation assembly can use a multi-axial screw assembly 10 at one or more locations along the length of the spine. The spinal fixation assembly can be used in a variety of applications within the spine to address a wide range of spinal pathologies. For example, a fixation assembly can be limited to the lumbar region for fixation following a diskectomy. Alternatively, a spinal fixation assembly can extend substantially along the entire length of the spine, such as along the thoracic and lumbar regions, to correct a deformity, such as scoliosis.

In other applications, a spinal fixation assembly implementing the present invention can provide for fixation and stabilization of the cervical spine, such as might occur following a fracture or dislocation. It is of course understood by a person of skill in this art that the components of the spinal fixation system will vary depending upon the region of the spine, and the treatment to be administered. In certain applications, a number of hooks will engage aspects of several vertebrae. In another fixation assembly, bone screws can be threaded into portions of the vertebrae, as all operating as an anchor for an elongated member, such as a spinal rod.

In accordance with the present invention, engagement between the elongated member and one or more vertebrae may require orientation of a fixation member at a wide range of three dimensional angles relative to the elongated member. In some circumstances, it is difficult to situate the elongated member, such as a spinal rod, in an optimum location relative to the vertebrae. In this instance, engagement of a fixation member to the spine may require that the fixation member assume various angles relative to the spinal rod, and certainly angles that may not be achieved by prior devices and systems.

Figure 3:
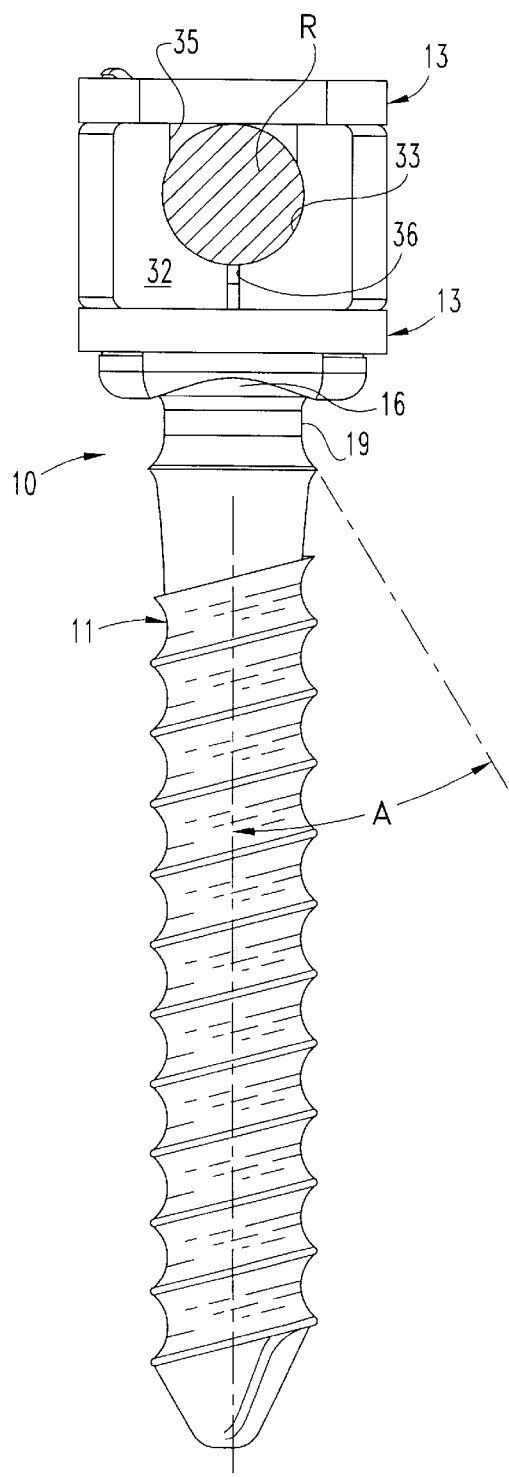
FIG. 3 is a side elevational view of the screw assembly shown in FIG. 1, with a spinal rod engaged within the assembly.
Figure 4:
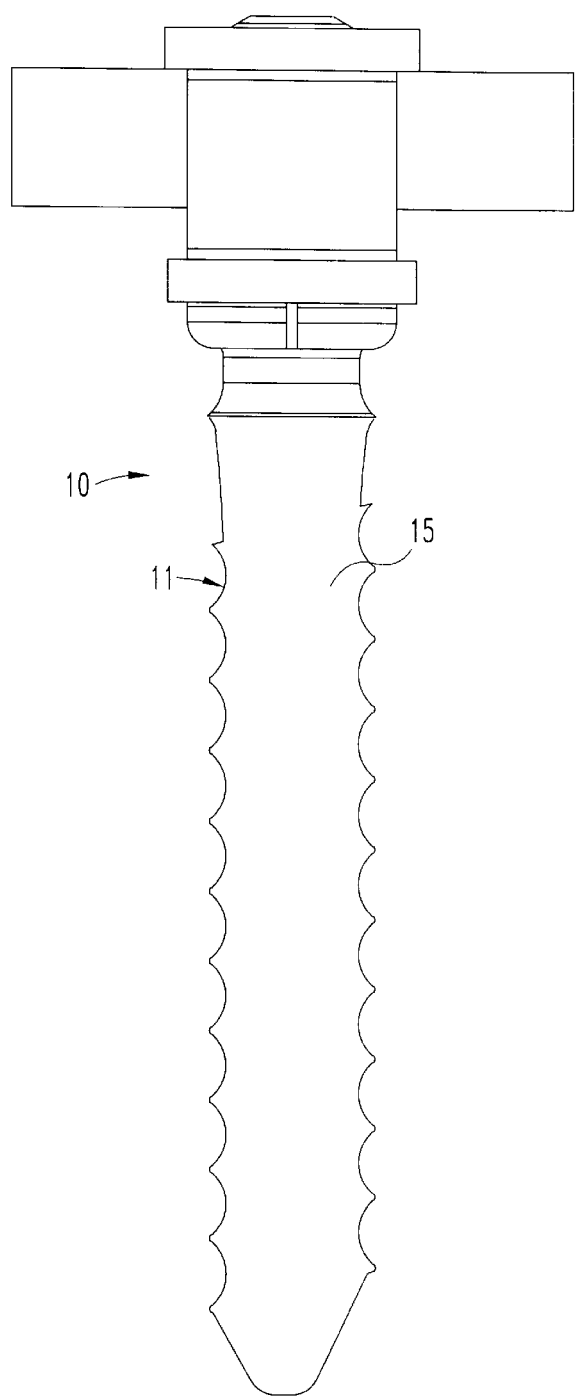
FIG. 4 is a side elevational view of the assembly as shown in FIG. 3, with the assembly rotated 90° to show the rod extending through the multi-axial screw assembly.
Figure 10:
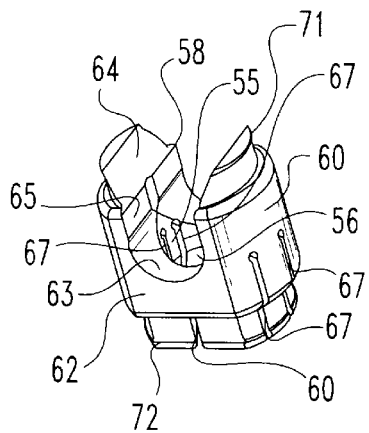
FIG. 10 is a top perspective view of a receiver member according to an additional embodiment of the invention.
Figure 11:
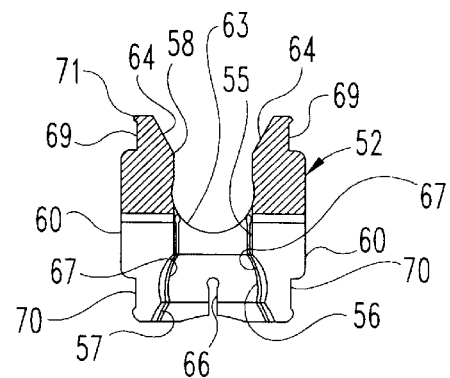
FIG. 11 is a cross-sectional view of the receiver member depicted in FIG. 10.
Figure 12:
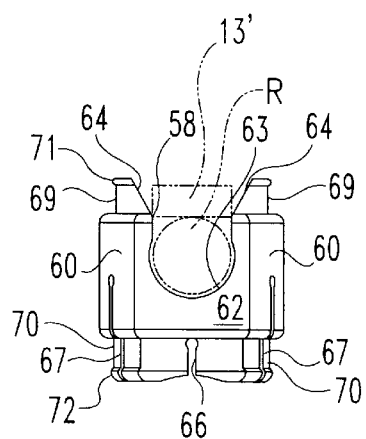
FIG. 12 is a side elevational view of the receiver member shown in FIG. 10, with a spinal rod and SMA ring depicted in phantom lines engaged to the receiver member.
Figure 13:
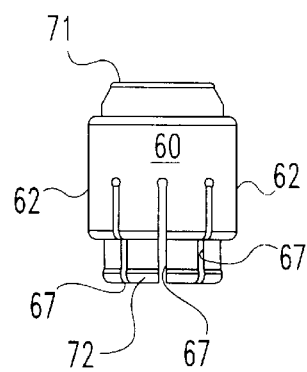
FIG. 13 is an end elevational view of the receiver member shown in FIG. 10.

Referring now to FIGS. 1 and 2, a multi-axial screw assembly 10 according to one embodiment of the invention is illustrated. The assembly 10 includes a bone screw 11 that is mounted within a receiver member 12. In the preferred embodiment, a pair of shape-memory alloy (SMA) locking rings 13 are provided to clamp the receiver member 12 about at least the bone screw 11. A use of the screw assembly 10 as part of a spinal fixation system is depicted in FIGS. 3 and 4. In this particular spinal fixation system or assembly, the elongated member is a spinal rod R that extends through the receiver member 12. As shown specifically in FIG. 3, the bone screw 11 is capable of assuming a range of angles up to an angle A relative to the spinal rod. It is understood that the bone screw can sweep through a cone defined at the angle A, although the angle is only depicted in the plane of the paper in the figure.

Details of the bone screw 11 are shown in FIG. 5. In particular, the bone screw 11 includes a threaded shank 15 that carries threads configured to engage the bone of a vertebra. In one specific embodiment, the threads can be cancellous threads that are configured to engage the vertebral body. The bone screw 11 also includes a head 16 that is preferably at least partially spherically shaped. In one specific embodiment, the head 16 includes a flat surface 16a within which is defined a tool receiving recess 17. The tool receiving recess 17 can be configured to accept any type of known driving tool. In the specific embodiment, the tool receiving recess 17 is a hex recess to receive the hex end of a driving tool. The tool receiving recess 17 allows for insertion of the bone screw 11 into the vertebra.

The head 16 of bone screw 11 is preferably substantially spherically shaped to include a spherical surface 18. The spherical surface 18 provides for bearing contact with the receiver member 12 so that the bone screw can be arranged at a variety of angular orientations relative to the receiver member, with and without the spinal rod R extending therethrough. In a further aspect of the bone screw 11, an annular relief 19 is provided between the spherical head 16 and the threaded shank 15. Referring back to FIGS. 1 and 2, it can be seen that that annular relief 19 allows the bone screw 11 to have a wider range of movement within the receiver member 12 and helps avoid contact between the shank of the bone screw and the bottom of the receiver member.

Details of the receiver member 12 can be discerned from FIGS. 6–8. In one specific embodiment, the receiver member 12 defines a spherical recess 26 adjacent the bottom end of the member. The recess is preferably at least partially spherical, as shown more clearly in FIG. 2. In the specific embodiment, the spherical recess 26 has a diameter that is substantially equal to the diameter of the spherical surface 18 of the head of the bone screw 11. In addition, in the specific embodiment, the spherical recess 26 contacts only a portion of the spherical surface 18 of the bone screw 11. In the illustrated embodiment, this contact amounts to about one-third of the spherical surface 18.

Returning to FIGS. 6–8, it can be seen that the receiver member 12 includes a flared opening 27 at the bottom of the member. Again looking back to FIG. 2, this flared opening 27 can be seen as providing for an enhanced range of movement of the bone screw 11 as the spherical head 16 pivots within the spherical recess 26. In accordance with the preferred embodiment, the flared opening 27 communicates with the spherical recess 26 at a diameter that is less than the largest diameter of the spherical head 16 of the bone screw 11. In this manner, the bone screw 11 will not pass through the bottom of receiver member 12.

In one embodiment, the receiver member further defines a central bore 25 extending from the top of the member to the recess 26. In this specific embodiment, the central bore 25 has a diameter that is approximately equal to the diameter of the spherical recess 26, or more particularly the diameter of the head 16 of the bone screw 11. The bone screw can be inserted into the receiver member 12 through an upper opening 28. The screw 11 passes through the bore 25 so that the head 16 of the bone screw can be pressed into the spherical recess 26 at the base of bore 25. As also shown in FIG. 2, the bore 25 can also allow access for a driving tool to engage the tool receiving recess 17 of the bone screw 11. In this manner, the bone screw can be threaded into a vertebra with the screw provisionally retained within the receiver member 12.

Looking again at FIGS. 6–8, it can be seen that the receiver member 12 has the general configuration of a cylinder having truncated side walls. In the preferred embodiment, the receiver member 12 includes opposite curved side walls 30 separated by opposing flat side walls 32. The flat side walls 32 define a rod channel 33 that extends transversely across bore 25 in the receiver member 12. An angled guide wall 34 can be formed on top of each of the curved side walls 30 to guide a spinal rod R (FIG. 3) through the upper opening 28 and into the rod channel 33. In accordance with a specific embodiment, the rod channel 33 is substantially circular and has a diameter that is substantially equal to the outer diameter of the spinal rod R to be disposed within the channel. The flat side walls 32 also define a linear channel 35 communicating between the rod channel 33 and the upper opening 28. Preferably, the linear channel 35 defines a width that is slightly smaller than the diameter of the rod channel 33 and than the largest diameter of the spinal rod R to be disposed within the rod channel 33. In this manner, the spinal rod can be at least provisionally held within the rod channel 33 prior to tightening of the locking rings 13 about the receiver member 12. In a specific embodiment, the width of the linear channel 35 is less than the diameter of the bore 25.

The preferred embodiment contemplates a receiver member 12 that is split at a pair of opposite upper slots 36 and a pair of opposite lower slots 37. In one embodiment, the upper slots 36 are defined from the base of the rod channel 33. The upper slots 36 permit slight contraction of the upper portion of the receiver member 12 about a spinal rod R disposed within the rod channel 33. Moreover, the upper slots 36 also permit slight expansion of the receiver member and particular the bore 25 during insertion of the bone screw 11 and linear channel 35 during insertion of the rod R from the upper opening 28.

In the present embodiment, the lower slots 37 are disposed at the bottom of the receiver member 12 and intersect the flared opening 27 and the spherical recess 26, in accordance with the preferred embodiment. The lower slots 37 allow contraction of the lower portion of the receiver member 12 about the head 16 of the bone screw 11. As shown in FIGS. 6–8, the upper slots 36 are offset by 90° relative to the lower slots 37. More particularly, the upper slots 36 are defined in the flat side walls 32, while the lower slots 37 are defined in the curved side walls 30.

In the preferred embodiment, the receiver member 12 defines features for supporting the pair of SMA locking rings 13. In one specific embodiment, an upper engagement groove 39 is defined within the curved side walls 30 at the top of the receiver member 12. A lower engagement groove 40 is also defined in the curved side walls 30 at the bottom of the receiver member 12. Preferably, the upper and lower grooves 39, 40 are configured to closely receive a corresponding locking ring 13 thereabout. An upper lip 41 is provided at the upper end of the engagement groove 39 to retain a locking ring 13 at the top of receiver member 12. Likewise, a lower lip 42 helps retain a locking ring 13 at the bottom of the receiver member 12.

In the specific embodiment of the invention, the lower engagement groove 40 is situated within the same plane as the spherical recess 26. In this manner, when the locking ring 13 at the bottom of the receiver member 12 contracts, the greatest amount of force will be applied directly from the receiver member 12 through the recess 26 to the spherical head 16 of the bone screw 11. Again in the specific embodiment, the upper engagement groove 39 is situated as close to the top of the receiver member 12 as possible so that upon contraction of the upper locking ring 13, the receiver member 12 wraps slightly around the spinal rod R to clamp the rod within the rod channel 33.

In one feature of the present invention, each of the locking rings 13 has a substantially similar configuration. As shown in FIG. 9, the locking rings 13 are substantially rectangular with curved end walls to substantially conform to the truncated cylindrical configuration of the receiver member 12. In other words, each of the locking rings 13 includes opposite curved walls 45 separated by opposite flat walls 46. Preferably, the locking rings 13 define an opening 47 between the walls 45, 46 that conforms to the upper engagement groove 39 and lower engagement groove 40. Also preferably, the ring 13 has an effective diameter between the curved walls 45 that is substantially equal to the diameter of the engagement grooves 39, 40 when the SMA locking ring 13 is in its martensitic or room temperature state.

When the locking ring 13, and particularly the screw assembly 10, is placed within the patient, the body temperature of the patient will increase the temperature of the locking rings 13. As the temperature increases past the transformation temperature range, the locking rings 13 move from their martensitic to their austenitic phases. In the austenitic phase at the higher temperature, the locking rings 13 deform to a smaller size, as reflected by the curved walls 45' and flat walls 46'. The locking ring 13 in the upper groove 39 can be formed so that only the flat walls 46 shorten, while locking ring for the lower groove 40 can be formed so that only the curved walls 45 shorten. In this manner, the curved walls 45 of the upper locking ring can press the curved side walls 30 of the receiver member 12 toward each other and about the spinal rod R as the flat walls shorten. Likewise, the shortening of the curved walls 46 of the lower locking ring can cause the side walls 46 of the ring to press the side walls 32 of the receiver member 12 together about the screw head.

In accordance with the present invention, the multi-axial screw assembly 10 is initially provided with the spherical head 16 of the bone screw 11 disposed within the spherical recess 26 of the receiver member 12. In addition, a locking ring 13 is situated within the lower engagement groove 40 to loosely retain the bone screw within the receiver member.

This initially assembled arrangement can be introduced to the surgical site and the bone screw 11 threaded into the vertebra according to the protocol for the particular spinal procedure. As indicated above, a driving tool can pass through the bore 25 of the receiver member 12, with the bore being substantially aligned with the tool receiving recess 17 in the head of the bone screw. Preferably, the bone screw 11 is driven into the vertebra to a recommended depth for adequate fixation, but preferably not so deep that the bottom of the receiver member 12 will contact or press against the vertebral bone. In order for the multi-axial capability of the assembly 10 to be realized, the receiver member 12 must be free to pivot in three dimensions about the head 16 of the bone screw 11.

Once the bone screw has been adequately fixed within the vertebra, the spinal rod R can be introduced into the rod channel 33, as shown in FIG. 3. It should be noted that the receiver member 12 is configured so that the spinal rod R does not contact the bone screw 11, regardless of the relative angle between the rod, receiver member 12 and bone screw head 16. Instead, the rod R is supported in the rod channel 33 by the flat side walls 32. With the rod properly positioned, the second locking ring 13 can be disposed on the receiver member 12, and particularly in the upper engagement groove 39.

It is understood that the locking rings 13 are at least initially at or below room temperature. Once the first locking ring 13 is situated within the patient upon insertion of the bone screw 11, the temperature of the locking ring 13 and the lower engagement groove 40 will increase. Once that temperature increases beyond the transformation temperature range of the SMA, the locking ring 13 will contract to the shape shown in FIG. 9 as indicated by curved walls 45' and flat walls 46'. At this point, the spherical head 16 of the bone screw 11 will be firmly clamped within the spherical recess 26 of the receiver member 12.

Substantially concurrently, the locking ring 13 in the upper engagement groove 39 will also contract as its temperature increases above the transformation temperature range. At that point, then, the receiver member 12 will be contracted about the spinal rod R to firmly clamp the spinal rod within the rod channel 33. Once both SMA locking rings 13 have moved to their austenitic phase, the multi-axial screw assembly 10 is firmly clamped and the bone screw 11 is solidly fixed to the spinal rod R. It can be seen that the present invention provides a screw assembly 10 that offers a low profile and minimum prominence. In particular, the bone screw is attached to the spinal rod directly beneath the rod, or in line between the rod and the vertebra. The overall bulk or prominence of the present invention is minimized by the use of the SMA locking rings 13, which is in contrast to the prior devices which require some form of external cap or nut threaded onto the top of a receiver member.

The present invention provides a screw assembly that can be tightened from the top, meaning that the bone screw 11 can be threaded onto the vertebra from the top. In addition, the spinal rod is loaded from the top, which can greatly simplify a spinal surgical procedure. In accordance with one feature of the invention, the rod does not need to be preloaded into the receiver member 12. Moreover, the multi-axial capability allows a bone screw to be connected with a spinal rod with minimal contouring of the rod being necessary.

In one specific embodiment of the invention, the bone screw 11 is configured for engagement in the lumbar spine and has an overall length of about 2.126 inches. The spherical head 16 and particularly the spherical surface 18 of the bone screw has an outer diameter of about 0.315 inches, while the annular relief 19 has a diameter of about 0.236 inches.

Further in accordance with a specific embodiment, the receiver member 12 has an overall height of about 0.609 inches. The receiver member defines a bore 25 having a diameter of about 0.295 inches, which is slightly smaller than the outer diameter of the spherical head 16 of the bone screw 11. On the other hand, the spherical recess 26 has a diameter of approximately 0.315 inches to correspond to the outer diameter of the head of the bone screw 11. The flared opening 27 of the receiver member 12 increases to an opening diameter of 0.400 inches, in the specific embodiment. Also in the specific embodiment, the receiver member 12 has a width between the flat side walls 32 of 0.354 inches. This corresponds to the room temperature distance between the flat walls 46 of the locking rings 13. Similarly, the receiver member 12 has a maximum dimension between the curved side walls 30 of 0.462 inches at the upper and lower engagement grooves 39, 40. This dimension is substantially the same as the maximum distance between the curved walls 45 of the locking rings 13 in their room temperature configuration.

In the preferred embodiment, the upper slots 36 and lower slots 37 have a width of about 0.020 inches, which means that the receiver member 12 can contract over that distance at the respective slots. Thus, in order for the receiver member 12 to contract at the slots 36, 37 extent, the flat walls 46 of the locking rings 13 must shrink by about 0.020 inches. This change in length amounts to about a 4% reduction in the overall length of each of the flat walls 46. This percentage reduction is typical for many medical grade SMAs; however, other SMAs could be used having different transformation capabilities. In the specific embodiment, the locking rings 13 are formed of Nitinol®.

In an alternative embodiment of the invention, a modified receiver member 52 is provided as shown in FIGS. 10–13. In this embodiment, the receiver member 52 includes a bore 55 extending through a small portion of the center of the receiver member. The bore opens into a spherical recess 56 that is configured so that the recess has a maximum diameter that is larger than the maximum diameter of the bore 55. In one specific embodiment, the recess has a diameter of about 0.320 in. to accomodate a similarly sized bone screw head, while the bore 55 has a diameter of about 0.250 in.

The recess 56 is only partially spherical, meaning that it does not extend entirely around the spherical head of a bone screw disposed within the recess. The recess 56 opens to the bottom of the receiver member at a flared opening 57. In the present embodiment, the recess contacts about half of the surface area of the bone screw, with the greater amount of contact at the upper hemisphere of the recess. In one specific embodiment, the recess 56 intersects the bore 55 at the bore's diameter of 0.250 in. At the lower end of the recess, the recess 56 intersects the flared opening 57 at a diameter that is greater than the diameter of the bore, namely about 0.305 in.

An upper opening 58 is provided at the top end of the receiver member, in one specific embodiment, preferably to permit insertion of the spinal rod. In this alternative embodiment, the bone screw, which can be the bone screw 11 described above, is loaded into the receiver member 52 from the bottom of the member. Thus, the upper opening 58 need not be provided for insertion of the bone screw, as in the embodiment of FIGS. 1–9. Likewise, the bore 55 may be eliminated unless it is needed for access by a screw insertion tool.

In accordance with this alternative embodiment, the receiver member 52 includes curved side walls 60 and flat side walls 62 similar to the receiver member 12. Likewise, the member 52 includes a rod channel 63 defined in the side walls that intersects a portion of the bore 55. The rod channel 63 opens to a linear channel 65 that incorporates angled guide walls 64 at the top end of the receiver member. In this embodiment, the linear channel 65 has a width that is substantially equal to the diameter of the bore 55 and rod channel 63.

As in the previous embodiment, the receiver member 52 is adapted to receive SMA locking rings at the top and bottom of the member. Thus, the receiver member 52 includes upper and lower engagement grooves 69, 70 defined by upper and lower lips 71, 72. An SMA locking ring 13 fits into each of the grooves 69, 70 and operates in the thermally responsive manner described above to contract about the receiver member.

In a further modification from the prior embodiment, the receiver member 52 includes short slots 66 defined in the flat side walls 62, and long slots extending from the bottom of the receiver in the curved side walls 60. In accordance with the present embodiment, the one short slot is provided in each flat side wall 62 that emanates from the bottom of the receiver member and that terminates generally in the middle of the spherical recess 56. On the other hand, the three long slots are provided in the curved side walls 60. The long slots extend from the bottom of the receiver member and terminate adjacent the level of the bottom of the rod channel 63.

The receiver member 52 of the embodiment in FIGS. 10–13 permits bottom loading of the bone screw by brief expansion of the spherical recess 56 and flared opening 57 at the slots 66 and 67. The lower SMA locking ring 13 can be added once the bone screw head is situated within the recess 56 by slightly compressing the receiver member at the slots 66, 67. Contraction of the lower SMA locking ring 13 due to temperature change again operates to compress the receiver member at the lower engagement groove 70 by closing the slots. In one specific embodiment, only the short slots 66 in the flat side walls 62 will close to clamp the bone screw head within the spherical recess 56. In another embodiment, the long slots 67 will also collapse upon a size reduction of the SMA locking ring.

Fixation of a spinal rod within the receiver member of this embodiment can be accomplished in many ways. First, referring to FIG. 12, it can be seen that an SMA locking ring 13' disposed in the upper engagement groove 69 will directly abut the rod R' disposed within the rod channel 63. In this respect, the upper groove 69 and locking ring 13' is situated closer to the rod channel 63, and consequently the spinal rod R', than with the previous embodiment. Fixation of the rod R' within the rod channel 63 can also be effected by compression of the upper portion of the receiver member, and particularly the upper portion of the curved side walls 60, by SMA contraction of the upper locking ring 13'. Finally, additional compression of the receiver member 52 can be accomplished by contraction of the SMA locking ring in the lower engagement groove which contract the slots 66 and 67.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

For example, while the preferred embodiment contemplates a bone screw, such as screw 11, other bone engaging fasteners are contemplated. The multi-axial capabilities can be equally applicable to a vertebral hook, for example. Further, the components of the multi-axial screw assembly 10 can be sized according to the portion of the spine within which the assembly is to be used. In the illustrated embodiment, the components are dimensioned for use in the lumbar spine. It is understood that smaller components would be required in the thoracic and cervical spine, while the multi-axial movement capabilities can be equally well suited throughout the entire length of the spine. Further, while the invention is described for engagement to an elongated cylindrical rod, other elongated members are contemplated.

What is claimed:

1. A spinal fixation assembly comprising:
   an elongated member configured for placement adjacent the spine;
   a bone engaging fastener, said fastener having a lower portion configured for engaging a vertebra and a head, said head being at least partially spherical in configuration;
   a receiver member having a top end and an opposite bottom end, said receiver member defining a recess for receiving said head of said bone engaging fastener therein, said recess having a lower opening at said bottom end of said receiver member through which said lower portion of said fastener extends, said receiver member also including a channel having an upper opening at said top end of said receiver member, said channel being configured to receive said elongated member therein;
   a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about said head of said bone engaging fastener within said recess;
   said recess is disposed within said receiver member adjacent said bottom end thereof; and
   said receiver member defines an outer annular lower groove adjacent said bottom end, said groove configured to receive said compression member when said compression member is in said first configuration.

2. The spinal fixation assembly according to claim 1, wherein:
   said receiver member includes an outer annular upper groove adjacent said top end thereof; and
   said assembly includes a second compression member configured to be received within said upper groove.

3. The spinal fixation assembly according to claim 2, wherein said second compression member is formed of a shape memory material having a first configuration to be received within said upper groove at substantially said first temperature and a different second configuration at substantially said different second temperature in which said second compression member contracts about said receiver member.

4. A spinal fixation assembly comprising:
   an elongated member configured for placement adjacent the spine;
   a bone engaging fastener, said fastener having a lower portion configured for engaging a vertebra and a head, said head being at least partially spherical in configuration;
   a receiver member having a top end and an opposite bottom end, said receiver member defining a recess for receiving said head of said bone engaging fastener therein, said recess having a lower opening at said bottom end of said receiver member through which said lower portion of said fastener extends, said receiver member also including a channel having an upper opening at said top end of said receiver member, said channel being configured to receive said elongated member therein;
   a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about said head of said bone engaging fastener within said recess;
   said receiver member includes opposite first side walls defining said channel and opposite second side walls intermediate said first side walls;
   said receiver member includes a first slot defined in each of said opposite second side walls, each said first slot extending from said bottom end toward said top end of said receiver member; and
   said receiver member includes a second slot defined in each of said opposite first side walls, each said second slot extending from said channel toward said bottom end of said receiver member.

5. The spinal fixation assembly according to claim 4, wherein each said second slot intersects said recess.

6. The spinal fixation assembly according to claim 5, wherein each said second slot terminates at said recess.

7. The spinal fixation assembly according to claim 4, wherein each said first slot intersects said recess.

8. The spinal fixation assembly according to claim 7, wherein each said first slot terminates at said recess.

9. The spinal fixation assembly according to claim 4, wherein each said second slot intersects said recess; and
   each said second slot terminates between said recess and said top end of said receiver member.

10. The spinal fixation assembly according to claim 9, wherein each said second slot terminates adjacent said channel.

11. The spinal fixation assembly according to claim 10, wherein each said second slot intersects said recess.

12. An assembly for engaging a bone engaging fastener having a head to an elongated member, said assembly comprising:
    a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;
    a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said receiver member includes an outer annular upper groove adjacent said top end thereof; and said assembly includes a second compression member configured to be received within said upper groove.

13. The spinal fixation assembly according to claim 12, wherein said second compression member is formed of a shape memory material having a first configuration to be received within said upper groove at substantially said first temperature and a different second configuration at substantially said different second temperature in which said second compression member contracts about said receiver member.

14. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said recess is disposed within said receiver member adjacent said bottom end thereof; and said receiver member defines an outer annular upper groove adjacent said top end, said groove configured to receive said compression member when said compression member is in said first configuration.

15. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said recess is disposed adjacent said bottom end of said receiver member;

said channel is disposed adjacent said top end of said receiver member and is disposed apart from said recess so that the head of the bone engaging fastener does not intersect said channel when the head is disposed within said recess;

said assembly further includes a second compression member formed of a shape memory material having a first configuration at substantially said first temperature and a different second configuration at substantially said different second temperature in which said second compression member contracts about said receiver member; and said receiver member defines an outer annular upper groove adjacent said top end thereof, said upper groove configured to receive said second compression member therein when said second compression member is in said first configuration, whereby said second compression member contracts about said receiver member in said different second configuration to compress said receiver member about the elongated member disposed within said channel.

16. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said receiver member includes opposite first side walls defining said channel and opposite second side walls intermediate said first side walls; and said receiver member includes a second slot defined in each of said opposite first side walls, each said second slot extending from said channel toward said bottom end of said receiver member.

17. The spinal fixation assembly according to claim 16, wherein each said second slot intersects said recess; and each said second slot terminates between said recess and said top end of said receiver member.

18. The spinal fixation assembly according to claim 17, wherein each said second slot terminates adjacent said channel.

19. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said receiver member includes opposite first side walls defining said channel and opposite second side walls intermediate said first side walls; and said opposite first side walls are substantially flat and said opposite second walls are curved.

20. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said receiver member further defines a bore extending from said top end of said receiver and communicating with said recess, said bore intersecting said channel and having a bore diameter;

the elongated member is a rod having a rod diameter, wherein said channel has a channel diameter substantially equal to the rod diameter; and said bore diameter is greater than said channel diameter.

21. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess;

said receiver member further defines a bore extending from said top end of said receiver and communicating with said recess, said bore intersecting said channel and having a bore diameter;

said receiver member further defines a flared opening from said recess to said bottom end of said receiver member; and said flared opening intersects said recess at a lower diameter substantially equal to said bore diameter.

22. An assembly for engaging a bone engaging fastener having a head to an elongated member, said assembly comprising:

a receiver member having a top end and an opposite bottom end, said receiver member defining a recess for receiving the head of the bone engaging fastener therein, said recess having a lower opening at said bottom end of said receiver member through which a lower portion of the fastener extends, said receiver member also including a channel having an upper opening at said top end of said receiver member, said channel being configured to receive the elongated member therein;

a compression member disposed around a portion of said receiver member, said compression member being formed of a shape memory material and having a first configuration at a first temperature and a different second configuration at a different second temperature in which said compression member contracts about said portion of said receiver member to thereby compress said receiver member about the head of the bone engaging fastener within said recess, wherein:

said receiver member defines a groove; and said compression member is a ring sized to fit within said groove.

23. The spinal fixation assembly according to claim 22, wherein:

a portion of said groove is flat and a remaining portion of said groove is curved; and said ring includes flat and curved portions substantially corresponding to said flat and curved portions of said lower groove.

24. The spinal fixation assembly according to claim 23, wherein said ring is a closed ring that entirely encircles said receiver member at said groove.

* * * * *